(12) United States Patent
Muller et al.

(10) Patent No.: US 6,858,731 B1
(45) Date of Patent: Feb. 22, 2005

(54) PROCESS FOR THE PREPARATION OF PURE STEREOISOMERS OF TETRAHYDROFOLIC ACID ESTERS SALTS AND TETRAHYDROFOLIC ACID BY FRACTIONATED CRYSTALLIZATION OF TETRAHYDROFOLIC ACID ESTERS SALTS

(75) Inventors: Hans Rudolf Muller, Schaffhausen (CH); Rudolf Moser, Schaffhausen (CH); Viola Groehn, Neuhausen am Rheinfall (CH)

(73) Assignee: EPROVA AG, Schaffhausaen (CH)

( * ) Notice: Subject to any disclaimer, the term of this patent is extended or adjusted under 35 U.S.C. 154(b) by 7 days.

(21) Appl. No.: 10/030,693

(22) PCT Filed: Jul. 12, 2000

(86) PCT No.: PCT/EP00/06647

§ 371 (c)(1),
(2), (4) Date: Jan. 14, 2002

(87) PCT Pub. No.: WO01/04121

PCT Pub. Date: Jul. 12, 2000

(30) Foreign Application Priority Data

Jul. 14, 1999 (CH) ............................................. 1300/99

(51) Int. Cl.$^7$ ..................... C07D 475/04; C07D 425/04
(52) U.S. Cl. ....................................... 544/258; 544/261
(58) Field of Search ................................. 544/258, 261

(56) References Cited

U.S. PATENT DOCUMENTS

| 5,006,655 A | | 4/1991 | Müller et al. ............... 544/258 |
|---|---|---|---|
| 5,300,503 A | | 4/1994 | Peake et al. ................. 514/250 |
| 5,324,836 A | * | 6/1994 | Muller et al. ............... 544/258 |
| 5,489,684 A | * | 2/1996 | Jequier et al. .............. 544/258 |
| 5,698,693 A | * | 12/1997 | Fitzhugh et al. ............ 544/258 |
| 6,271,374 B1 | | 8/2001 | Müller et al. ............... 544/258 |
| 6,596,721 B2 | | 7/2003 | Müller et al. ............... 514/249 |
| 2001/0002398 A1 | | 5/2001 | Müller et al. ............... 514/249 |

FOREIGN PATENT DOCUMENTS

| EP | 0 348 641 A2 | 1/1990 |
|---|---|---|
| EP | 0348641 | 1/1990 |
| EP | 0 495 204 A1 | 7/1992 |
| EP | 0495204 | 7/1992 |
| EP | 0 537 492 A1 | 4/1993 |
| EP | 0537492 | 4/1993 |
| EP | 0 682 026 A1 | 11/1995 |
| EP | 0682026 | 11/1995 |

* cited by examiner

*Primary Examiner*—Richard L. Raymond
*Assistant Examiner*—Tamthom N. Truong
(74) *Attorney, Agent, or Firm*—Millen White Zelano & Branigan, P.C.

(57) ABSTRACT

A process for preparing and concentrating (6S,αS) or (6S, αR) tetrahydrofolic acid ester salts and (6S,αS) or (6S,αR) tetrahydrofolic acid, characterized by preparing or dissolving equimolar or concentrated mixtures of diastereomers of addition salts of tetrahydrofolic acid esters with aromatic sulphonic acids in organic solvents, followed by crystallizing them at least once, and then if applicable hydrolyzing the crystallizate to produce (6S,αS) or (6S,αR) tetrahydrofolic acid, crystallizing the latter as a free acid or isolating it in the form of a salt.

16 Claims, No Drawings

PROCESS FOR THE PREPARATION OF PURE STEREOISOMERS OF TETRAHYDROFOLIC ACID ESTERS SALTS AND TETRAHYDROFOLIC ACID BY FRACTIONATED CRYSTALLIZATION OF TETRAHYDROFOLIC ACID ESTERS SALTS

The present invention relates to a process for preparing and concentrating (6S,αS) or (6S,αR) tetrahydrofolic acid ester salts and (6S,αS) or (6S,αR) tetrahydrofolic acid by preparing or dissolving equimolar or concentrated mixtures of diastereomers of addition salts of tetrahydrofolic acid esters with aromatic sulphonic acids in an organic solvent, followed by crystallising them at least once, and if applicable hydrolysing them to produce (6S,αS) or (6S,αR) tetrahydrofolic acid and crystallising these as the free acid or isolating them in the form of their salts. The addition salts of the (6R,αS) or (6R,αR) tetrahydrofolic acid esters can be isolated with the corresponding sulphonic acids from the mother liquor and the corresponding tetrahydrofolic acids or their salts obtained by hydrolysis.

Folic acid is depicted in formula I,

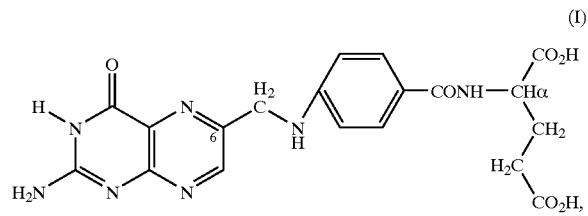

where the asymmetric α-C atom may be present in the glutaminic acid residue in the S configuration (αS) or in the R configuration (αR). Hereinafter the enantiomers of folic acid will be referred to as (αS) folic acid and (αR) folic acid. The same goes for the folic acid esters and their derivatives. They will be referred to as (αS) folic acid esters and (αR) folic acid esters. Naturally occurring folic acid corresponds to (αS) folic acid.

Tetrahydrofolic acid is depicted in formula II,

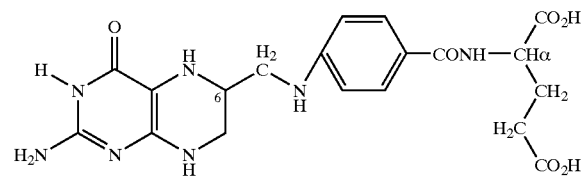

where the asymmetric α-C atom may be present in the glutaminic acid residue in the S configuration (αS) or in the R configuration (αR), and the asymmetric C atom 6 in the tetrahydropterin radical may be present in the S configuration (6S) or R configuration (6R). Hereinafter the diastereomers of tetrahydrofolic acid will be referred to as (6S,αS), (6S,αR), (6R,αS) and (6R,αR) tetrahydrofolic acid. The same goes for the tetrahydrofolic acid esters and their derivatives. They will be referred to as (6S,αS), (6S,αR), (6R,αS) and (6R,αR) tetrahydrofolic acid esters. Naturally occurring tetrahydrofolic acid corresponds to (6S,αS) tetrahydrofolic acid.

Hereinafter the term folic acid, folic acid esters and folic acid ester salts, unless designated otherwise, always embraces the two enantiomers (αS) and (αR) and the term tetrahydrofolic acid, tetrahydrofolic acid esters and tetrahydrofolic acid ester salts embraces all possible diastereomers.

Tetrahydrofolic acid has found broad therapeutic application in the form of 5-formyl or 5-methyl derivatives and their physiologically compatible salts. It has long been known that the biological activity of naturally occurring diastereomers of the reduced folates, e.g. of (6S,αS) tetrahydrofolic acid, is by far the most vigorous. Therefore it makes sense to provide therapeutic preparations that contain only the most active form or in which the latter is at least highly concentrated.

On an industrial scale tetrahydrofolic acid is generally made by heterogeneous hydrogenation of the two imino groups in the pterin skeleton of (αS) folic acid, usually obtaining an equimolar mixture of (6S,αS) tetrahyrdrofolic acid and (6R,αS) tetrahydrofolic acid. The equimolar mixture can be used for pharmaceutical formulations. Beforehand, however, it is also possible to concentrate the desired (6S,αS) diasteromer of tetrahydrofolic acid by fractionated crystallisation or to recover it in pure form, for which various processes are known; for example see EP-0 495 204.

The process described in EP-0 495 204 uses the equimolar mixtures of (6S,αS) and (6R,αS) diastereomers of tetrahydrofolic acid sulphonic acid salts, which are dissolved in water and then crystallised. This process results in concentration of the desired (6S,αS) diastereomers, it being possible to already achieve very high concentrations in the first crystallisation step (up to about 95%) and to obtain pure (6S,αS) tetrahydrofolic acid by a further fractionated crystallisation. This process is not a serious contender, inter alia from the economic viewpoint, since the sulphonic acids used for the salt formation can only be isolated from aqueous mother liquors with great effort, and it therefore becomes necessary to dispose of large volumes of mother liquors containing sulphonic acid, which is uneconomical.

EP-0 682 026 describes the preparation of stable crystalline (6S,αS) and (6R,αS) tetrahydrofolic acid by crystallisation from an aqueous medium at certain pHs. However, the concentrations in the case of the fractionated crystallisations are so low that multiple steps are necessary to concentrate the desired diastereomer to above 99.5%. This entails major substance losses and the risk of forming chemical breakdown products. The use of this process for concentrating synthetic isomers is especially laborious.

Surprisingly, it has been found that aromatic sulphonic acid salts (addition salts) of tetrahydrofolic acid esters are eminently suited to the preparation of optically pure diastereomers of tetrahydrofolic acid because only the addition salts of the (6S,αS) or (6S,αR) diastereomer crystallise out from organic solvents. Starting from a 70:30 isomer mixture, even a first crystallisation produces an unusually high concentration, perhaps even above 99%, of the (6S,αS) or (6S,αR) diastereomer, respectively, or mixtures thereof in the crystallisate, and of the (6R,αS) or (6R,αR) diastereomer, respectively, or mixtures thereof in the mother liquor. With a further crystallisation it is then normally possible to obtain the optically pure diastereomers.

The subject matter of the invention is a process for preparing and concentrating (6S,αS) or (6S,αR) tetrahydrofolic acid ester salts and (6S,αS) or (6S,αR) tetrahydrofolic acid, characterised by preparing or dissolving equimolar or concentrated mixtures of diastereomers of addition salts of tetrahydrofolic acid esters with aromatic sulphonic acids in organic solvents, followed by crystallising them at least once, and then, if applicable, hydrolysing the crystallisate to produce (6S,αS) or (6S,αR) tetrahydrofolic acid, crystallising the latter as a free acid or isolating it in the form of a salt.

Within the framework of the invention, crystallising at least once means fractionated crystallisation to the desired purity. The number of crystallisation steps will be determined chiefly according to how much of the desired diastereomer(s) is contained in the starting product.

The addition salts of the tetrahydrofolic acid esters may be of formula III and embrace the (6S,αS), (6S,αR), (6R,αS) and (6R,αR) diastereomers,

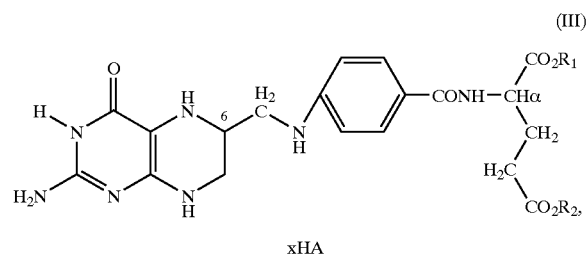

xHA in which $R_1$ or $R_2$ denotes H, and one of $R_1$ or $R_2$, or both $R_1$ and $R_2$ independently of one another represent a monovalent hydrocarbon radical or a heterohydrocarbon radical attached via a C atom, with heteroatoms selected from the group comprising —O—, —S— and —N—, HA stands for an aromatic sulphonic acid, and x denotes an integer from 1 to 6 or a fractional number between 0 and 6.

$R_1$ and $R_2$ may be selected independently of one another, but they are preferably identical. It is preferred that $R_1$ and $R_2$ represent a hydrocarbon radical. With $R_1$ and $R_2$ as a hydrocarbon radical, the radicals concerned may be aliphatic radicals having 1 to 20 carbon atoms, preferably 1 to 12, more especially 1 to 8, and most preferably 1 to 4 carbon atoms, cycloaliphatic or cycloaliphatic-aliphatic radicals having 3 to 8 cyclic hydrocarbon atoms and 1 to 6 carbon atoms in the aliphatic radical, aromatic hydrocarbon radicals with 6 to 14 carbon atoms, more especially 6 to 10 carbon atoms, or aromatic-aliphatic radicals having 7 to 15 carbon atoms, more especially 7 to 10 carbon atoms.

The heterohydrocarbon radical may be heteroalkyl having 2 to 16 carbon atoms, preferably 2 to 10 carbon atoms, and more especially 2 to 6 carbon atoms, heterocycloaliphatic radicals having 3 to 8, preferably 5 or 6 ring links, heterocycloaliphatic-aliphatic radicals having 3 to 8, preferably 5 or 6 ring links, and 1 to 6, preferably 1 to 4 carbon atoms in the aliphatic radical, heteroaromatic radicals having preferably 4 to 13 carbon atoms, and more especially 4 to 9 carbon atoms and at least one heteroatom, and heteroaromatic-aliphatic radicals having preferably 4 to 13 carbon atoms, and more especially 4 to 9 carbon atoms and at least one heteroatom, and 1 to 6, preferably 1 to 4 carbon atoms in the aliphatic radical, where the hetero radicals contain at least one hetero atom selected from the group —O—, —S— and —N— and preferably —O— and —N—.

The hydrocarbon radicals may for example be selected from the group comprising linear and branched $C_1$–$C_{20}$ alkyl, $C_3$–$C_8$ cycloalkyl and preferably $C_4$–$C_7$ cycloalkyl, $C_3$–$C_8$ cycloalkyl-$C_1$–$C_6$ alkyl and preferably $C_4$–$C_7$ cycloalkyl-$C_1$–$C_4$ alkyl, $C_6$–$C_{10}$ aryl or $C_7$–$C_{12}$ aralkyl.

The heterohydrocarbon radicals may for example be selected from the group comprising $C_2$–$C_{16}$ heteroalkyl, $C_2$–$C_7$ heterocycloalkyl and preferably $C_4$–$C_5$ heterocycloalkyl, $C_4$–$C_7$ heterocycloalkyl-$C_1$–$C_6$ alkyl and preferably $C_4$–$C_5$ heterocycloalkyl $C_1$–$C_6$ alkyl, $C_4$–$C_9$ heteroaryl and preferably $C_4$–$C_5$ heteroaryl, and $C_5$–$C_{12}$ heteroaralkyl and preferably $C_5$–$C_{10}$ heteroaralkyl, where the hetero radicals contain 1 to 3, preferably 1 or 2, heteroatoms from the group comprising —O— and —N—.

$R_1$ and $R_2$ may be linear or branched alkyl which preferably contains 1 to 12 carbon atoms, more especially 1 to 8, and most preferably 1 to 4 carbon atoms. Examples are methyl, ethyl, and the isomers of propyl, butyl, pentyl, hexyl, heptyl, octyl, decyl, dodecyl, tetradecyl, hexadecyl, octadecyl and eicosyl. The alkyl is preferably linear and the alkyl is preferably methyl, ethyl, n-propyl and n-butyl. It is most preferred of all if alkyl stands for methyl.

As cycloalkyl, $R_1$ and $R_2$ contain preferably 4 to 7 and most preferably 5 or 6 cyclic hydrocarbon atoms. Examples of cycloalkyl are cyclopropyl, cyclobutyl, cyclopentyl, cyclohexyl, cycloheptyl and cyclooctyl. Cyclohexyl is especially preferred.

As cycloalkyl alkyl, $R_1$ and $R_2$ contain preferably 4 to 7 and most preferably 5 or 6 cyclic hydrocarbon atoms, and preferably 1 to 4 and most preferably 1 or 2 carbon atoms in the aliphatic radical. Examples of cycloalkyl alkyl are cyclopropyl methyl or cyclopropyl ethyl, cyclobutyl methyl or cyclobutyl propyl, cyclopentyl methyl oder cyclopentyl ethyl, cyclohexyl methyl oder cyclohexyl ethyl, cycloheptyl methyl and cyclooctyl methyl. Cyclohexyl methyl or cyclohexyl ethyl is especially preferred.

As aryl, $R_1$ and $R_2$ may stand for naphthyl and preferably for phenyl. As aralkyl, $R_1$ and $R_2$ are preferably phenyl alkyl having preferably 1 to 4 carbon atoms in the alkyl. Examples are benzyl and β-phenyl ethyl.

As heteroalkyl, $R_1$ and $R_2$ may for example be $C_1$–$C_4$-alkyl-X1-$C_2$–$C_4$-alkyl, where $X_1$ stands for O or $NC_1$–$C_4$-alkyl. Examples are methoxy ethyl and ethoxy ethyl.

As heterocycloalkyl, $R_1$ and $R_2$ may for example be pyrrolidinyl, piperidinyl, morpholinyl, tetrahydropyranyl or piperazinyl.

As heterocycloalkyl alkyl, $R_1$ and $R_2$ may for example be pyrrolidinyl methyl or pyrrolidinyl ethyl, piperidinyl methyl or piperidinyl ethyl, morpholinyl methyl or morpholinyl ethyl, tetrahydropyranyl methyl or tetrahydropyranyl ethyl or piperazinyl methyl or piperazinyl ethyl.

As heteroaryl, $R_1$ and $R_2$ may for example be thiophenyl, furanyl, pyranyl, pyrrolyl, imidazolyl, pyridinyl, pyrimidinyl, pyrazinyl, indolyl, quinolinyl, oxazolyl or isooxazolyl.

As heteroaralkyl, $R_1$ and $R_2$ may for example be furanyl methyl or furanyl ethyl, pyranyl methyl or pyranyl ethyl, pyrrolyl methyl or pyrrolyl ethyl, imidazolyl methyl or imidazolyl ethyl, pyridinyl methyl or pyridinyl ethyl, pyrimidinyl methyl or pyrimidinyl ethyl, pyrazinyl methyl or pyrazinyl ethyl, indolyl methyl or indolyl ethyl, quinolinyl methyl or quinolinyl ethyl.

A preferred group of formula III compounds are those in which $R_1$ and $R_2$ independently of one another represent $C_1$–$C_4$ alkyl, $C_5$ cycloalkyl oder $C_6$ cycloalkyl, phenyl, $C_1$–$C_4$ alkyl phenyl, benzyl or $C_1$–$C_4$-akyl benzyl. $R_1$ and $R_2$ are preferably identical radicals. It is most preferred of all if $R_1$ and $R_2$ represent $C_1$–$C_4$ alkyl, for example methyl or ethyl.

In formula III, x preferably denotes an integer or fractional number from 0.5 to 4, more especially an integer or fractional number from 0.5 to 3, and most especially an integer or fractional number from 0.5 to 2.

The aromatic sulphonic acids may contain one to three, preferably one or two, and more especially one sulphonic acid group. Sulphonic acids of aromatic hydrocarbons are preferred. The aromatic sulphonic acids may be unsubstituted or substituted with halogen, linear or branched $C_1$–$C_8$ alkyl, preferably $C_1$–$C_4$ alkyl, linear or branched $C_1$–$C_8$ alkoxy, preferably $C_1$–$C_4$ alkoxy, and linear or branched $C_1$–$C_8$ haloalkyl, preferably $C_1$–$C_4$ haloalkyl. Some examples of substituents are methyl, ethyl, propyl, butyl, methoxy, ethoxy, trifluoromethyl or trichloromethyl, fluorine and chlorine. The aromatic radical preferably contains a substituent. Phenyl and naphthyl are preferred among the aromatic groups.

The aromatic sulphonic acids most preferably are of formula IV,

$$R_3\text{—}SO_3H \qquad (IV),$$

in which $R_3$ represents phenyl, unsubstituted or substituted with F, Cl, Br, $C_1$–$C_4$ alkyl $C_1$–$C_4$ haloalkyl or $C_1$–$C_4$ alkoxy. Some specific examples of $R_3$ are phenyl, methyl phenyl, fluorophenyl, chlorophenyl, tichloromethyl phenyl and trifluoromethyl phenyl.

Especially preferred formula III compounds are those in which $R_1$ and $R_2$ each represent methyl, x stands for 1 or 2 or for a fractional number between 0.5 and 2, and HA denotes phenylsulphonic acid, toluylsulphonic acid, fluorosulphonic acid, chlorosulphonic acid or trifluoromethylphenyl sulphonic acid. Preferred substituted radicals are p-toluylmethyl phenyl, p-fluoromethyl phenyl, p-chloromethyl phenyl or p-trifluoromethyl phenyl.

The most preferred formula III compounds of all are those in which $R_1$ and $R_2$ each represent methyl, x stands for 1 or 2 or for a fractional number between 0.5 and 2, and HA denotes phenylsulphonic acid or p-toluylsulphonic acid.

The addition salts of the tetrahydrofolic acid esters used in accordance with the invention are novel and may for example be prepared by esterification of tetrahydrofolic acid in the presence of sulphonic acids, or by esterification of tetrahydrofolic acid salts in a polar organic solvent.

It is also possible to start from folic acid, and to hydrogenate the latter with hydrogen in a per se known manner in the presence of heterogeneous or homogeneous hydrogenation catalysts. The hydrogenation may also be performed diastereoselectively if hydrogenation is carried out with hydrogen in a polar reaction medium, for example an aqueous or alcoholic reaction medium, in the presence of chiral hydrogenation catalysts that are soluble in the reaction medium. Suitable hydrogenation catalysts are known. In particular these are metal complexes of Rh, Ir or Ru with ditertiary diphosphines, as for example described by H. Brunner and W. Zettlmeier, Handbook of Enantioselective Catalysis, Vol. II: Ligand References, published by VCH Verlagsgesellschaft mbH, Weinheim (1993). The resulting tetrahydrofolic acid may subsequently be esterified in a per se known manner. If hydrogenation takes place in an alcohol as solvent and in the presence of a sulphonic acid under reaction conditions that result in esterification of the folic acid, this results directly in the addition salts from the corresponding tetrahydrofolic acid esters and sulphonic acids.

Alternatively, however, it is possible to start from folic acid esters, and to hydrogenate these in a per se known manner with hydrogen in the presence of heterogeneous or homogeneous hydrogenation catalysts. The hydrogenation may also be performed diastereoselectively if hydrogenation is carried out with hydrogen in a polar reaction medium, for example an alcoholic reaction medium, in the presence of chiral hydrogenation catalysts that are soluble in the reaction medium. The resulting tetrahydrofolic acid esters can subsequently be converted with sulphonic acids into addition salts. Hydrogenation may be carried out as described earlier, using alcohol-soluble metal complexes of Ir, Rh or Ru and ditertiary diphosphines as hydrogenation catalysts. If the hydrogenation takes place in an alcohol as solvent and in the presence of a sulphonic acid, this results directly in the addition salts from the corresponding tetrahydrofolic acid esters and sulphonic acids. If addition salts from folic acid esters with sulphonic acids are used for the hydrogenation, this likewise results directly in the addition salts of tetrahydrofolic acid esters and sulphonic acids.

Equimolar or concentrated mixtures within the framework of the invention are taken to mean mixtures that either contain identical amounts of diastereomers with the (6S) and (6R) configuration or a surplus of a diastereomer with the (6S) or (6R) configuration. It also possible to employ mixtures of diastereomers with the (6S) and (6R) configuration that have either the (αS) or (αR) configuration, or mixtures of diastereomer pairs with the (6S) and (6R) configuration and a different configuration at the α-C atom. The mixtures may respectively contain the (6S,αS) or (6S, αR) diastereomers in a proportion of at least 5%, preferably at least 20%, and most preferably at least 30% and up to around 75% or more.

Suitable organic solvents are polar organic solvents that are preferably able to dissolve at least 1 g of addition salt of a tetrahydrofolic acid ester per liter of solvent at boiling temperature. Examples of solvents are halohydrocarbons (methylene chloride, chloroform, tetrachloroethane, chlorobenzene); ethers (diethylether, dibutylether, tetrahydrofuran, dioxan, ethylene glycol dimethyl ether or ethylene glycol diethyl ether); carboxylic acid esters and lactones (methyl acetate, ethyl acetate, methyl propionate, valerolactone); N,N-substituted carboxylic acid amides and lactams (dimethyl formamide, dimethyl acetamide, N-methyl pyrrolidone); ketones (acetone, methyl isobutyl ketone, cyclohexanone); sulphoxides and sulphones (dimethyl sulphoxide, dimethyl sulphone, tetramethylene sulphone); and alcohols (methanol, ethanol, n-propanol or i-propanol, n-butanol, i-butanol or t-butanol, pentanol, hexanol, cyclohexanol, cyclohexanediol, hydroxymethyl cyclohexane or dihydroxymethyl cyclohexane, benzyl alcohol, ethylene glycol, diethylene glycol, propanediol, butanediol, ethylene glycol monomethyl ether or ethylene glycol monoethyl ether, and diethylene glycol monomethyl ether or diethylene glycol monoethyl ether. Ethanol and especially methanol are preferred. Mixtures of at least two solvents may also be used.

It is especially preferred to use alcohols or blends of alcohols with at least one further solvent. The proportion of an alcohol preferably amounts to at least 30%, more especially at least 50% and most preferably at least 70% by volume. Most preferred of all is the use of alcohol alone, for example methanol, or blends of alcohol with alcohol-miscible solvents, for example methanol with ethers.

Specifically the process may be carried out by for example mixing equimolar or concentrated mixtures of diastereomers from addition salts of tetrahydrofolic acid esters and aromatic sulphonic acids with a solvent and subsequently heating the mixture to dissolve the addition salts of tetrahydrofolic acid esters and aromatic sulphonic acids. Heating may be carried out up to the boiling temperature of the solvent. After this the solution is cooled down to no further than the point at which a solvent solidifies, whereupon the (6S,αS) or (6S,αR) diastereomers or both diastereomers crystallise out, either spontaneously or by seeding with the desired diastereomer or diastereomers, or else by concentrating the solution by evaporation, and can then be separated in the usual manner by filtration.

It has proved to be particularly advantageous that for the preparation or concentration of the addition salts of tetrahydrofolic acid esters with aromatic sulphonic acids it is also possible to directly use the reaction solutions from the hydrogenation of folic acid esters, or from the hydrogenation of addition salts of folic acid esters and aromatic sulphonic acids.

Starting from a 70:30 isomer mixture, an extremely high concentration is already observed in the first crystallisation, which, in an entirely surprising manner, may for example be more than 99%. Consequently, fewer crystallisation steps are now needed in order to prepare the pure (6S,αS) or (6S,αR) diastereomers, for example up to three, yet surprisingly often only a single crystallisation step.

The degree to which the (6S,αS) or (6S,αR) diastereomers are observed to be concentrated in the crystallisate is so high and the crystallising capacity of these isomers so excellent that the process according to the invention can even be employed to isolate (6S,αS) or (6S,αR) diastereomers from mother liquors that contain predominately (6R, αS) or (6R,αR) diastereomers. The method according to the invention is eminently suited to separation processes on an industrial scale.

The addition salts of (6S,αS) or (6S,αR) tetrahydrofolic acid esters with sulphonic acids obtained following separation can subsequently be hydrolysed in a per se known manner, for example using bases such as NaOH or KOH. The corresponding (6S,αS) or (6S,αR) tetrahydrofolic acids are accordingly obtained. These tetrahydrofolic acids can be isolated in a stable form as free acids by crystallisation, as for example described in EP-A-0 682 026. By adding acids, for example sulphonic acids, the salts of the tetrahydrofolic acids can likewise be crystallised and further concentrated if desired (EP-0 495 204).

The examples which follow can be carried out with similar success by replacing the generically or specifically described reactants and/or process conditions of this invention with ones that are set out in the following examples. Similarly, the following specific exemplary embodiments are given by way of example only and are not to be regarded as in any way limiting the remainder of the disclosure.

The overall disclosure includes all applications, patents and publications cited in this text by virtue of making reference thereto.

On the basis of the foregoing description it will be possible for anyone skilled in the field to readily deduce the decisive elements of the invention and, without deviating from the underlying concept and the scope of the invention, to make alterations and supplements to it and thereby adapt the invention to different needs and conditions.

The following abbreviations are used:

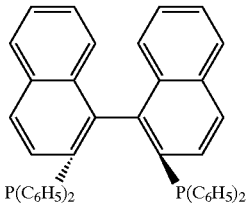

(R-BINAP)

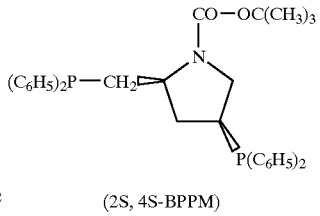

(2S, 4S-BPPM)

and COD stands for cyclooctadiene.

The optical yield, or the ratio of the (6S,αS) diastereomer to the (6R,αS) diastereomer or of the (6S,αR) diastereomer to the (6R,αR) diastereomer, is determined in the following manner using high-pressure liquid chromatography directly in the crystallisate or in the mother liquor: 0.5 mg of the crystallisate or 15 mg of the mother liquor are dissolved in 1 ml of solvent prepared from 6.8 g of β-cyclodextrin and 270 ml of 37% formaldehyde in 1000 ml of water. The separation is done by means of a 5 mm, 240×4 mm Nucleosil C-8 column made by the firm Macherey-Nagel and a mobile solvent prepared in the following manner: 6.8 g of β-cyclodextrin are dissolved in a mixture of 8.5 ml of triethylamine, 850 ml of water and 150 ml of acetonitrile. The pH of the solution is adjusted to pH 7.5 by addition of acetic acid, and a further 270 ml of 37% formaldehyde are added. The detection of the diastereomers takes place at a wavelength of 300 nm.

The preparation and concentration of the solutions and the suspensions, as well as the transfer thereof, takes place under exclusion of oxygen, and using protective gases such as, for example, nitrogen or inert gases.

EXAMPLES

A Preparing solutions of addition salts from tetrahydrofolic acid esters and sulphonic acids Example A1 a Preparation of (αS) folic acid dimethylester benzene sulphonate 800 g of (αS) folic acid dihydrate (1.68 mmoles) are charged at 40° C. into a solution of 530 g of benzene sulphonic acid (3.35 mmoles) and 20 liters of anhydrous methanol in a nitrogen atmosphere. The mixture is heated for half an hour with refluxing, cooled down and concentrated by evaporation to a volume of 5 liters. The precipitate is filtered off by suction, washed with 1 liter of methanol and dried in a drying chamber at 40° C. and 20 mbars. 966 g of (αS) folic acid dimethylester benzene sulphonate are obtained (1.45 mmole, 86% of theoretical yield). The product contains 26.2% benzene sulphonic acid, 1.67% water and 2.26% methanol.

The substance breaks down above 150° C.

$^1$H-NMR in DMSO-d6: 8.78 (1 H, s), 8.46 (2H, bs), 8.32 (1H, d), 7.64–7.68 (m), 7.35–7.40 (m), 6.66 (2H, d), 0.8 (2H, s), 4.39 (1H, m), 3.62 (3H, s), 3.57 (3H, s), 2.42 (2H, m), 1.98–2.11 (2H, m).

b Preparation of a solution of a (6S,αS)/(6R,αS) diastereomer mixture of tetrahydrofolic acid dimethylester benzene sulphonate by hydrogenation of (αS) folic acid dimethylester benzene sulphonate 6.72 mg [Ir(COD)Cl]2 (10 μmoles) and 15.57 mg (25 μmoles) of R-BINAP are weighed, degassed and dissolved in dichloromethane. Dichloromethane is condensed off under a high vacuum and the residue is taken up in 5 ml of methanol. 1.25 g of (αS) folic acid dimethylester benzene sulphonate as per Example A1a (2 mmoles) are suspended in 25 ml of methanol and added to the catalyst. The suspension is added in a nitrogen countercurrent to a 100 ml autoclave and hydrogenated until the hydrogen uptake has ceased. COD stands for cyclooctadiene. Tetrahydrofolic acid dimethylester benzene sulphonate is obtained. The ratio of the diastereomers (6S,αS):(6R,αS) is 74:26.

c Preparation of a solution of a (6S,αS)/(6R,αS) diastereomer mixture of tetrahydrofolic acid dimethylester benzene sulphonate with a surplus of the (6R,αS) diastereomer by hydrogenation of (αS) folic acid dimethylester benzene sulphonate 6.72 mg [Ir(COD)Cl]2 (10 μmoles) and 13.84 mg (25 μmoles) of (2S,4S)-BPPM are weighed, degassed and dissolved in dichloromethane. Dichloromethane is condensed off under a high vacuum and the residue is taken up in 5 ml of methanol. 1.25 g of (αS) folic acid dimethylester benzene sulphonate as per Example A1a (2 mmoles) are suspended in 25 ml of methanol and added to the catalyst. The suspension is added in a nitrogen countercurrent to a 100 ml autoclave and hydrogenated for 17 hours. Tetrahydrofolic acid dimethylester benzene sulphonate is obtained. The ratio of the diastereomers (6S,αS):(6R,αS) is 34:66.

Example A2

Preparation of a solution of an equimolar (6S,αS)/(6R,αS) diastereomer mixture of tetrahydrofolic acid dimethylester benzene sulphonate by esterification of tetrahydrofolic acid 20 g of an equimolar mixture of (6S,αS) and (6R,αS) tetrahydrofolic acid (44.9 mmoles) are added to 10.65 g of benzene sulphonic acid (67.35 mmoles) in 900 ml of methanol and heated for 7 hours with refluxing. A solution of (6S,αS) and (6R,aS) tetrahydrofolic acid dimethylester benzene sulphonate is obtained.

Example A3

Preparation of a solution of a (6S,αS)/(6R,αS) diastereomer 70:30 mixture of tetrahydrofolic acid dimethylester benzene sulphonate by esterification of tetrahydrofolic acid in a (6S,αS)/(6R,αS) diastereomer ratio of 70:30

5.31 g of tetrahydrofolic acid (11.92 mmoles) in a 70:30 diastereomer ratio of (6S,αS):(6R,αS) (prepared as per EP 0 495 204 B1) are heated in 230 ml of methanol with 2.83 g of benzene sulphonic acid (17.88 mmoles) for 7 hours with refluxing. A solution of tetrahydrofolic acid dimethylester benzene sulphonate in a 70:30 diastereomer ratio of (6S,aS):(6R,aS) is obtained.

Example A4

Preparation of an equimolar solution of the diastereomers of (6S,αS) and (6R,αS) tetrahydrofolic acid dimethylester toluene sulphonate 10 g of an equimolar mixture of (6S,αS) and (6R,αS) tetrahydrofolic acid (22.45 mmoles) are added to 6.41 g of toluene sulfonic acid monohydrate (33.67 mmoles) in 450 ml of methanol and heated for 7 hours with refluxing. A solution of tetrahydrofolic acid dimethylester toluene sulphonate in a 1:1 diastereomer ratio of (6S,αS):(6R,αS) is obtained.

Example A5

Preparation of an equimolar solution of diastereomers of (6S,αS) and (6R,αS) tetrahydrofolic acid dimethylester naphthalino-1-sulphonate 3 g of an equimolar mixture of (6S,αS) and (6R,αS) tetrahydrofolic acid (6.73 mmoles) are added to 2.33 g of naphthalino-1-sulphonic acid sodium salt (10.1 mmoles) and 4.7 ml of 2 M HCl in 130 ml of methanol and heated for 7 hours with refluxing. A solution of tetrahydrofolic acid dimethylester naphthalino-1-sulphonate in a 1:1 diastereomer ratio of (6S,αS):(6R,αS) is obtained.

B Isolating and Concentrating Processes

Example B1

Isolation and concentration of (6S,αS) tetrahydrofolic acid dimethylester benzene sulphonate a The solution of tetrahydrofolic acid dimethylester benzene sulphonate obtained in accordance with Example A1b with a 74% proportion of the (6S,αS) diastereomer is concentrated by evaporation to 1/6 of the volume under exclusion of oxygen. The suspension thereby obtained is stored in a nitrogen atmosphere for 2 hours at 4° C., the precipitate is aspirated off, washed with a little cold methanol and dried at 40° C. and 20 mbars. 0.55 g of tetrahydrofolic acid dimethylester benzene sulphonate is obtained (0.87 mmole, 44% of theoretical yield). The ratio of the diastereomers of tetrahydrofolic acid dimethylester benzene sulphonate (6S,αS):(6R,αS) is 99:1. $[a]_{589}$=−69.8° (c=1 in dimethyl-sulphoxide).

The substance breaks down above 150° C.

$1^H$-NMR in DMSO-d6: 10.61 (1 H, bs), 8.35 (1H, d), 7.6–7.74 (m), 7.51 (1H, bs), 7.30–7.37 (m), 6.70 (2H, d, 2H, bs), 4.42 (2H, m), 3.63 (3H, s), 3.58 (3H, s) 3.50 (1H, m), 3.38 (1H, m), 3.28 (1H, m), 2.44 (2H, m), 2.01–2.13 (2H, m)

b Isolation and concentration of (6S,αS)-tetrahydrofolic acid dimethylester benzene sulphonate from the solution according to Example A1c The solution of tetrahydrofolic acid dimethylester benzene sulphonate obtained in accordance with Example A1c with a 34% proportion of the (6S,αS)-diastereomer is stored in a nitrogen atmosphere for 2 hours at 4° C., with exclusion of oxygen. Thereafter the precipitate is aspirated off, washed with a little cold methanaol and then dried at 40° C. and 20 mbars. 0.2 g of tetrahydrofolic acid dimethylester benzene sulphonate with a 96.6% proportion of the (6S,αS) diastereomer is obtained.

c Isolation and concentration of (6S,αS) tetrahydrofolic acid dimethylester benzene sulphonate from the solution according to Example A2

The clear solution from Example A2 is cooled down to room temperature and stirred overnight. The solid precipitate is aspirated off, washed with methanol and tert.-butylmethyl ether and dried at 30° C. and 10 mbars. 9.62 g of colourless crystalline tetrahydrofolic acid dimethylester benzene sulphonate (15.24 mmoles) with a 99.1% proportion of the (6S,αS) diastereomer are obtained (the (6R,αS) tetrahydrofolic acid dimethylester benzene sulphonate can be prepared from the mother liquor B1c as outlined in Example B5.)

4 g (6.34 mmoles) of the resulting tetrahydrofolic acid dimethylester benzene sulphonate with a 99.1% proportion of the (6S,αS) diastereomer are dissolved in 220 ml of boiling methanol. The solution is allowed to cool down to room temperature, left to stand overnight and the solid precipitate is aspirated off. It is washed with methanol and tert.-butyl methyl ether and dried at 35° C. and 10 mbars. 3.08 g (4.88 mmoles) of colourless crystalline tetrahydrofolic acid dimethylester benzene sulphonate with a 99.5% proportion of the (6S,(αS) diastereomer are obtained.

d Isolation and concentration of (6S,αS) tetrahydrofolic acid dimethylester benzene sulphonate from the solution according to Example A3

The solution obtained under Example A3 is allowed to cool to room temperature and the solution is seeded at 60° C. with diastereomer-pure (6S,αS) tetrahydrofolic acid dimethylester benzene sulphonate. After standing overnight the precipitated solid is aspirated off, washed with methanol and tert.-butyl methyl ether and dried at 35° C. and 10 mbars. 3.46 g (5.48 mmoles) of tetrahydrofolic acid dimethylester benzene sulphonate with a 99.9% proportion of the (6S,αS) diastereomer are obtained.

Example B2

Isolation and concentration of (6S,αS) tetrahydrofolic acid dimethylester toluene sulphonate The equimolar mixture of tetrahydrofolic acid dimethylester toluene sulphonate obtained under Example A4 is cooled down to room temperature and stirred overnight. The solid precipitate is aspirated off, washed with methanol and tert.-butyl methyl ether and dried at 30° C. and 10 mbars. 5.53 g of colourless crystalline tetrahydrofolic acid dimethylester toluene sulphonate (9.54 mmoles with a 99.1% proportion of the (6S,αS) diastereomer are obtained. 5.2 g (8.97 mmoles) of the tetrahydrofolic acid dimethylester toluene sulphonate obtained in this manner with a 99.1% proportion of the (6S,αS) diastereomer are dissolved in 182 ml of boiling methanol. The solution is allowed to cool down to room temperature, stirred for three hours at room temperature and the solid precipitate is aspirated off. It is washed with methanol and tert.-butyl methyl ether and dried at 35° C. and 10 mbars. 4.43 g (7.64 mmoles) of colourless crystalline tetrahydrofolic acid dimethylester toluene sulphonate with a 99.8% proportion of the (6S,αS) diastereomer are obtained.

Example B3

Isolation and concentration of (6S,αS) tetrahydrofolic acid dimethylester naphthalino-1-sulphonate The solution obtained under Example A5 is cooled down to room temperature and stirred overnight. The solid precipitate is aspirated off and dried at 30° C. and 10 mbars. 0.34 g of colourless tetrahydrofolic acid dimethylester naphthalino-1-sulphonate (0.55 mmole) with a 62.7% proportion of the (6S,αS) diastereomer is obtained.

Example B4

Preparation of (6S,αS) tetrahydrofolic acid benzene sulphonate by hydrolysis of tetrahydrofolic acid dimethylester benzene sulphonate 0.55 g of tetrahydrofolic acid dimethylester benzene sulphonate (0.95 mmole) in accordance with Example B1a and 0.32 g of sodium carbonate (3.02 mmoles) are dissolved in 4 ml of water under exclusion of oxygen. The solution is heated to 85° C. and after 30 minutes the pH is adjusted to pH 7.5 with 37% hydrochloric acid. 0.2 g of benzene sulphonic acid is added at 75° C. in 0.6 ml of water and then the pH is adjusted to pH 8 with 37% hydrochloric acid. The solution is allowed to cool down to room temperature and stirred for a further three hours. The product is filtered off by suction and dried for 4 days in a drying chamber at 30° C. and 20 mbars. 8.4 g of tetrahydrofolic acid benzene sulphonate are obtained (13.92 mmoles, 88% of theoretical yield).

The diastereomer ratio of the tetrahydrofolic acid benzene sulphonate (6S,αS):(6R,αS) is 99:1. The properties of the tetrahydrofolic acid benzene sulphonate are identical to those of the product described in EP 0495204 B1.

Example B5

Isolation of concentrated (6R,αS) tetrahydrofolic acid dimethylester benzene sulphonate The mother liquor from Example B1c is concentrated by evaporation to one-quarter of its volume. It is cooled down to 0° C., seeded with diastereomer-pure (6S,αS) tetrahydrofolic acid dimethylester benzene sulphonate, and 1.5 g of tetrahydrofolic acid dimethylester benzene sulphonate is aspirated off in a 97:3 ratio of (6S,αS):(6R,αS) diastereomers. The mother liquor is concentrated to dryness by evaporation. 200 ml of diethylether are added to the oily residue and this is stirred for 2 hours at 0° C. The solid precipitate is aspirated off, washed with diethyl ether and dried at 30° C. and 20 mbars. 14.8 g of tetrahydrofolic acid dimethylester benzene sulphonate in an 80:20 ratio of (6R,αS)/(6S,αS) diastereomer are obtained.

What is claimed is:

1. Process for preparing and concentrating (6S,αS) or (6S,αR) tetrahydrofolic acid ester salts and (6S,αS) or (6S,αR) tetrahydrofolic acid, comprising preparing or dissolving equimolar or concentrated mixtures of diastereomers of addition salts of tetrahydrofolic acid esters with aromatic sulphonic acids in organic solvents, followed by crystallizing them at least once, and then if applicable hydrolyzing the crystallizate to produce (6S,αS) or (6S,αR) tetrahydrofolic acid, crystallizing the latter as a free acid or isolating it in the form of a salt.

2. Process according to claim 1, wherein the addition salts of the tetrahydrofolic acid esters of formula III, which includes the (6S,αS), (6S,αR), (6R,αS) and (6R,αR) diastereomers,

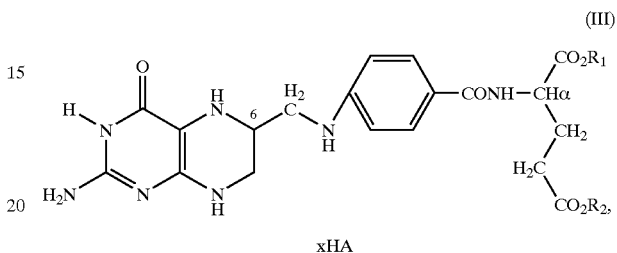

wherein $R_1$ and $R_2$, independently of one another, represent a monovalent hydrocarbon radical or a heterohydrocarbon radical attached via a C atom, with heteroatoms selected from the group —O—, —S— and —N—, or one of $R_1$ and $R_2$ is H, and the other is a monovalent hydrocarbon radical or a heterohydrocarbon radical defined above, HA stands for an aromatic sulphonic acid, and x denotes an integer from 1 to 6 or a fractional number between 0 and 6.

3. Process according to claim 1, wherein the aromatic sulphonic acids of formula IV,

in which $R_3$ represents unsubstituted phenyl or phenyl substituted with $C_1$–$C_4$ alkyl, $C_1$–$C_4$ haloalkyl or $C_1$–$C_4$ alkoxy.

4. Process according to claim 3, wherein one of the aromatic sulphonic acids is benzene sulphonic acid or p-toluene sulphonic acid.

5. Process according to claim 1, wherein the mixtures contain the (6S,αS) or (6S,αR) diastereomers respectively in a proportion of at least 5 percent by weight or more.

6. Process according to claim 1, wherein the organic solvents are polar organic solvents that dissolve at least 1 g of addition salt of a tetrahydrofolic acid ester per liter of solvent at a boiling temperature.

7. Process according to claim 1, wherein alcohols or mixtures of alcohols with at least one further solvent are used.

8. Process according to claim 1, further comprising providing a reaction solution from the hydrogenation of folic acid esters, or from the hydrogenation of addition salts of folic acid esters and aromatic sulphonic acids, or from the hydrogenation of folic acid in the presence of sulphonic acids.

9. A process for preparing and concentrating a (6S,αS) or (6S,αR) tetrahydrofolic acid ester salt or a (6S,αS) or (6S,αR) tetrahydrofolic acid, comprising preparing or dissolving an equimolar or a concentrated mixture of a diastereomer of an addition salt of a tetrahydrofolic acid ester with an aromatic sulphonic acid in an organic solvent, wherein the tetrahydrofolic acid ester is of the formula:

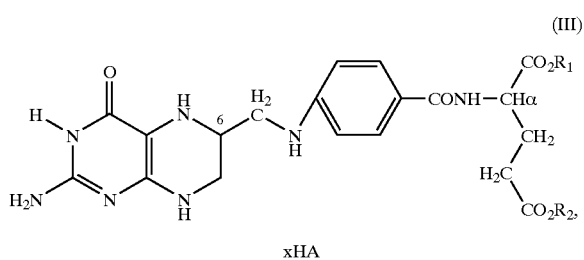

xHA $R_1$ and $R_2$, are independently, $C_1$–$C_4$ alkyl,

HA stands for the aromatic sulphonic acid, and x denotes an integer from 1 to 6 or a fractional number between 0 and 6, then crystallizing at least once, and optionally, hydrolyzing the crystallizate to produce (6S,αS) or (6S,αR) tetrahydrofolic acid, crystallizing the latter as a free acid or isolating the tetrahydrofolic acid in the form of a salt.

10. A process according to claim 3, wherein $R_1$ and $R_2$ are methyl.

11. A process for preparing and concentrating a (6S,αS) or (6S,αR) tetrahydrofolic acid ester salt or a (6S,αS) or (6S,αR) tetrahydrofolic acid, comprising preparing or dissolving an equimolar or a concentrated mixture of a diastereomer of an addition salt of a tetrahydrofolic acid ester with an aromatic sulphonic acid in an organic solvent, wherein the tetrahydrofolic acid or tetrahydrofolic acid ester is of the formula III,

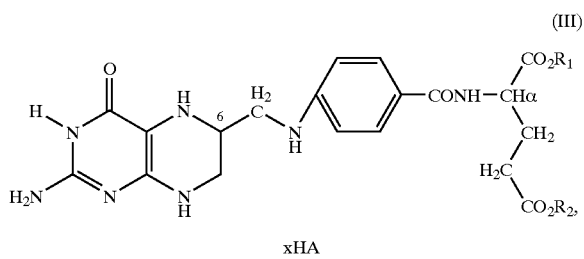

xHA wherein one of $R_1$ and $R_2$ is H and the other represents, or both $R_1$ and $R_2$, independently of one another represent, a monovalent hydrocarbon radical or a heterohydrocarbon radical attached via a C atom, wherein the heteroatom is —O—, —S—, or —N—, HA stands for the aromatic sulphonic acid, and x denotes an integer or a fractional number of 0.5–2.0, then crystallizing at least once, and optionally hydrolyzing the crystallizate to produce (6S,αS) or (6S,αR) tetrahydrofolic acid, crystallizing the latter as a free acid or isolating the tetrahydrofolic acid in the form of a salt.

12. A process according to claim 10, wherein in the formula III, x is 1 or 2 or a fractional number of 0.5–2, and HA is phenyl-, toluyl-, fluoro-, chloro- or trifluoromethylphenyl sulphonic acid.

13. A process according to claim 10, wherein in the formula III, x is 1 or 2 or a fractional number of 0.5–2, and HA is phenyl- or p-toluylsulphonic acid.

14. A process for preparing and concentrating a (6S,αS) or (6S,αR) tetrahydrofolic acid ester salt or a (6S,αS) or (6S,αR) tetrahydrofolic acid, comprising blending an equimolar or a concentrated mixture of a diastereomer of an addition salt from a tetrahydrofolic acid ester with an aromatic sulphonic acid in a solvent and then heating the mixture to dissolve the addition salt of the tetrahydrofolic acid or tetrahydrofolic acid ester and the aromatic sulphonic acid, thereafter cooling down the solution, whereupon the (6S,αS) or (6S,αR) diastereomer crystallizes out or both diastereomers crystallize out, and then separating the latter using filtration.

15. A process for preparing and concentrating a (6S,αS) or (6S,αR) tetrahydrofolic acid ester salt or a (6S,αS) or (6S,αR) tetrahydrofolic acid, comprising preparing or dissolving an equimolar or a concentrated mixture of a diastereomer of an addition salt of a tetrahydrofolic acid ester with an aromatic sulphonic acid in an organic solvent, followed by crystallizing at least once, and hydrolyzing with a base a (6S,αS) or (6S,αR) tetrahydrofolic acid or a mixture thereof, and crystallizing the tetrahydrofolic acid as a free acid or isolating the tetrahydrofolic acid in the form of a salt.

16. A process according to claim 1, wherein the addition salts of the tetrahydrofolic acid esters are of the formula III, which includes the (6S,αS), (6S,αR), (6R,αS) and (6R,αR) diastereomers,

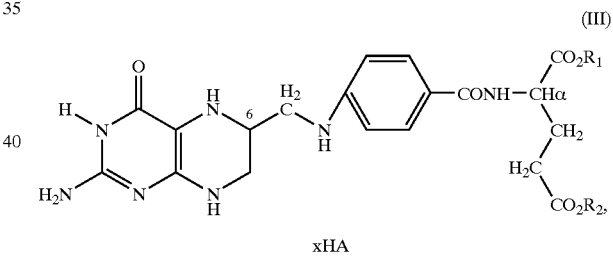

xHA wherein $R_1$ and $R_2$, independently of one another, represent a monovalent hydrocarbon radical or a heterohydrocarbon radical attached via a C atom, wherein the heteroatom is —O—, —S—, or —N—, HA stands for an aromatic sulphonic acid, and x denotes an integer from 1 to 6 or a fractional number between 0 and 6.

* * * * *

UNITED STATES PATENT AND TRADEMARK OFFICE
CERTIFICATE OF CORRECTION

PATENT NO. : 6,858,731 B1 Page 1 of 1
DATED : February 22, 2005
INVENTOR(S) : Hans Rudolf Müller et al.

It is certified that error appears in the above-identified patent and that said Letters Patent is hereby corrected as shown below:

Title page,
Item [54], Title, should read -- PROCESS FOR THE PREPARATION OF PURE STEREOISOMERS OF TETRAHYDROFOLIC ACID ESTER SALTS AND TETRAHYDROFOLIC ACID BY FRACTIONATED CRYSTALLISATION OF TETRAHYDROFOLIC ACID ESTER SALTS --.
Item [73], Assignee, "Schaffhausaen" should read -- Schaffhausen --.

Signed and Sealed this

Seventeenth Day of May, 2005

JON W. DUDAS
*Director of the United States Patent and Trademark Office*